US00PP17796P2

(12) United States Plant Patent
Addison

(10) Patent No.: US PP17,796 P2
(45) Date of Patent: Jun. 12, 2007

(54) ***MYOSOTIS* PLANT NAMED 'UNFORGETTABLE'**

(50) Latin Name: *Myosotis palustris*
Varietal Denomination: Unforgettable

(75) Inventor: Betty Ann Addison, Minneapolis, MN (US)

(73) Assignee: Witteman + Co., Hillegom (NL)

( * ) Notice: Subject to any disclaimer, the term of this patent is extended or adjusted under 35 U.S.C. 154(b) by 1 day.

(21) Appl. No.: 11/269,182

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Myosotis* plant named 'Unforgettable', characterized by its outwardly spreading to prostrate plant habit; freely branching growth habit; variegated leaves; and numerous bright blue-colored flowers.

1 Drawing Sheet

Botanical designation: *Myosotis palustris.*
Cultivar denomination: 'Unforgettable'.

BACKGROUND OF THE INVENTION

The present Invention relates to a new and distinct cultivar of *Myosotis* plant, botanically known as *Myosotis palustris,* and hereinafter referred to by the name 'Unforgettable'.

The new *Myosotis* is a naturally-occurring branch mutation of an unnamed selection of *Myosotis palustris,* not patented. The new *Myosotis* was discovered and selected by the Inventor in December, 1998 from within a population of plants of the parent selection in a controlled environment in Blaine, Minn.

Asexual reproduction of the new *Myosotis* by terminal cuttings in Blaine, Minn. since January, 1999, has shown that the unique features of this new *Myosotis* are stable and reproduced true to type in successive generations of asexual reproduction.

SUMMARY OF THE INVENTION

The following traits have been repeatedly observed and are determined to be the unique characteristics of 'Unforgettable'. These characteristics in combination distinguish 'Unforgettable' as a new and distinct cultivar:

1. Outwardly spreading to prostrate plant habit.
2. Freely branching growth habit.
3. Variegated leaves.
4. Numerous bright blue-colored flowers.

Plants of the new *Myosotis* differ from plants of the parent selection primarily in leaf coloration as plants of the parent selection do not have variegated leaves.

Plants of the new *Myosotis* can be compared to plants of the *Myosotis palustris* cultivar Snowflakes, not patented. In side-by-side comparisons conducted in north central Texas, plants of the new *Myosotis* differed from plants of the cultivar Snowflakes in the following characteristics:

1. Plants of the new *Myosotis* had variegated leaves whereas plants of the cultivar Snowflakes had solid green-colored leaves.

2. Plants of the new *Myosotis* and the cultivar Snowflakes differed in flower color as plants of the cultivar Snowflakes had white-colored flowers.

BRIEF DESCRIPTION OF THE PHOTOGRAPHS

The accompanying colored photographs illustrate the overall appearance of the new *Myosotis,* showing the colors as true as it is reasonably possible to obtain in colored reproductions of this type. Colors in the photographs may differ slightly from the color values cited in the detailed botanical description which accurately describe the colors of the new *Myosotis.*

The photograph at the top of the sheet comprises a top perspective view of typical plants of 'Unforgettable' grown in an outdoor nursery.

The photograph at the middle of the sheet is a close-up view of a typical plant of 'Unforgettable'.

The photograph at the bottom of the sheet is a close-up view of typical leaves of 'Unforgettable'.

DETAILED BOTANICAL DESCRIPTION

The new *Myosotis* has not been observed under all possible environmental conditions. The phenotype may vary somewhat with variations in environment such as temperature, daylength and light intensity, without, however, any variance in genotype.

The aforementioned photographs, following observations and measurements describe plants grown in Hillegom, The Netherlands, in an outdoor nursery and under commercial production practices. Plants were about two years old when the photographs and description were taken. During the production of the plants, day temperatures ranged from 18° C. to 32° C. and night temperatures ranged from 8° C. to 16° C. In the following description, color references are made to The Royal Horticultural Society Colour Chart, 2001 Edition, except where general terms of ordinary dictionary significance are used.

Botanical classification: *Myosotis palustris* cultivar Unforgettable.

Parentage: Naturally-occurring branch mutation of an unnamed selection of *Myosotis palustris,* not patented.

Propagation:

*Type.*—by cuttings.

*Time to initiate roots.*—About three weeks.

*Time to produce a rooted cutting.*—About four weeks.

*Root description.*—Fine, fibrous.

*Rooting habit.*—Freely branching.

Plant description:

*Plant form.*—Outwardly spreading to prostrate deciduous perennial.

*Growth habit.*—Moderately vigorous. Freely branching, about 24 lateral branches develop per plant.

*Plant height.*—About 25 cm.

*Plant width* (*spread*).—About 66 cm.

*Lateral branches.*—Length: About 24 cm. Diameter: About 4 mm. Internode length: About 7 mm. Strength: Strong. Texture: Densely pubescent; rough. Color: 138B.

*Foliage description.*—Arrangement: Alternate, simple; sessile. Length: About 3.7 cm. Width: About 1 cm. Shape: Elliptic to obovate. Apex: Rounded. Base: Attenuate. Margin: Entire. Texture, upper and lower surfaces: Densely pubescent; rough. Venation pattern: Pinnate. Color: Developing and fully expanded leaves, upper surface: 138A to 138B to 191A; towards the margins, 155A to 155B. Developing and fully expanded leaves, lower surface: 138B to 191A to 191B; towards the margins, 155A to 155B. Venation, upper and lower surfaces: Similar to lamina.

Flower description:

*Flower type/habit.*—Single, rounded salverform flowers arranged in terminal paired cymes; flowers face upright and outward. Freely flowering habit with about 1,200 flower buds and flowers per plant. Flowers not fragrant.

*Natural flowering season.*—Continuously flowering from June through September in The Netherlands. Flowers not persistent. Postproduction longevity: Flowers last two to three days on the plant.

*Inflorescence height.*—About 16.5 cm.

*Inflorescence diameter.*—About 7.3 cm.

*Flower buds.*—Height: About 4 mm. Diameter: About 2 mm. Shape: Obovate. Color: 76A to 76B.

*Flowers.*—Diameter: About 8.5 cm. Depth: About 5 mm.

*Petals.*—Quantity per flower: Typically five in a single whorl; petals fused at the base into a tube. Lobe length: About 6 mm. Lobe width: About 3 mm. Lobe shape: Spatulate. Apex: Broadly apiculate. Margin: Entire. Aspect: Mostly flat. Texture, upper and lower surfaces: Smooth, glabrous. Color: Developing petals, upper surface: 101B; towards the base, 21A to 21B. Developing petals, lower surface: 97B. Fully expanded petals, upper surface: 96C; towards the base, 21B. Fully expanded petals, lower surface: 97A.

*Sepals.*—Quantity per flower: Typically five in a single whorl, fused; campanulate calyx. Length: About 4 mm. Width: About 1.5 mm. Shape: Linear. Apex: Acute. Margin: Entire. Texture, upper and lower surfaces: Smooth, glabrous. Color, immature, upper and lower surfaces: 145A to 145B. Color, mature, upper and lower surfaces: 151D.

*Peduncles.*—Length: About 2.4 cm. Diameter: About 1.5 mm. Aspect: Mostly erect. Strength: Strong. Color: 138B.

*Pedicels.*—Length: About 3 mm. Diameter: About 0.5 mm. Aspect: Erect to about 80° from vertical. Strength: Strong. Color: 138B.

*Reproductive organs.*—Stamens: Quantity per flower: Typically five; fused with petals in tube. Filament length: About 1 mm. Anther shape: Oblong; curved. Anther length: About 0.7 mm. Anther color: 11A. Pollen amount: Scarce. Pollen color: 11A to 11B. Pistils: Quantity per flower: Typically one. Pistil length: About 2 mm. Stigma shape: Club-shaped. Stigma color: 150B. Style length: About 1.8 cm. Style color: 150C. Ovary color: 145B to 145C.

*Seed/fruit.*—Seed and fruit development have not been observed.

Disease/pest resistance: Plants of the new *Myosotis* have not been observed to be resistant to pathogens and pests common to *Myosotis.*

Temperature tolerance: Plants of the new *Myosotis* have been observed to tolerate high temperatures of 35° C. and are hardy to USDA Zone 6.

It is claimed:

1. A new and distinct cultivar of *Myosotis* plant named 'Unforgettable', as illustrated and described.

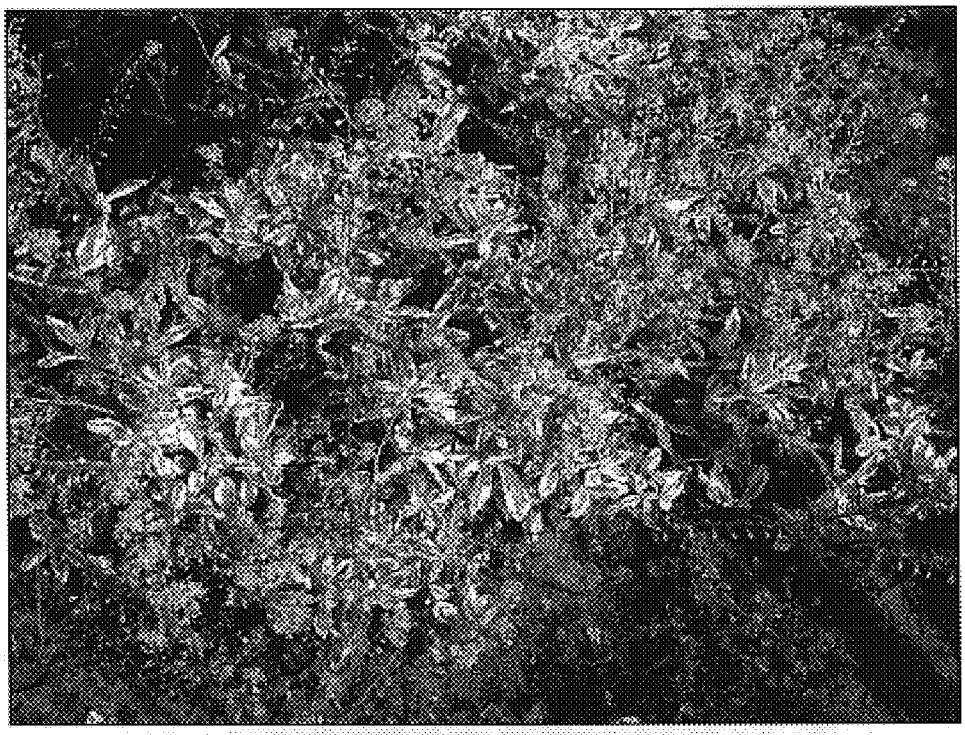
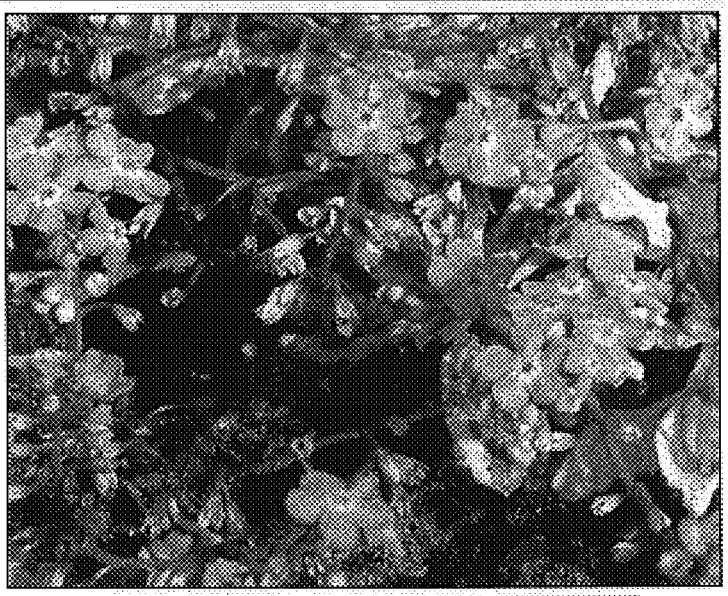
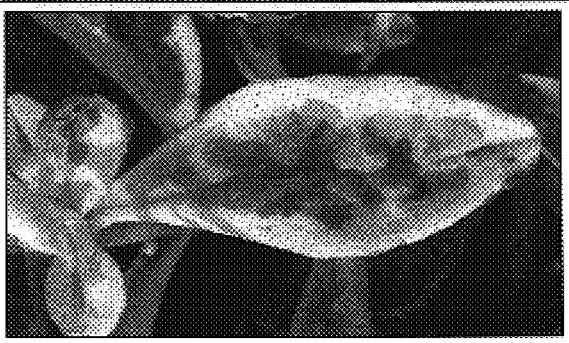

* * * * *